US006592556B1

(12) United States Patent
Thorne

(10) Patent No.: US 6,592,556 B1
(45) Date of Patent: Jul. 15, 2003

(54) MEDICAL NEEDLE SAFETY APPARATUS AND METHODS

(75) Inventor: David L. Thorne, Kaysville, UT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 09/619,190

(22) Filed: Jul. 19, 2000

(51) Int. Cl.[7] .............................................. A61M 5/32
(52) U.S. Cl. ...................................... 604/192; 604/110
(58) Field of Search ................................ 604/110, 192, 604/198, 263, 195, 240, 241, 243

(56) References Cited

U.S. PATENT DOCUMENTS

| | | | |
|---|---|---|---|
| 1,779,451 A | 10/1930 | Sponsel | |
| 2,559,474 A | 7/1951 | Son | 128/215 |
| 2,700,385 A | 1/1955 | Ortiz | 128/215 |
| 2,836,942 A | 6/1958 | Miskel | 53/25 |
| 2,854,976 A | 10/1958 | Heydrich | 128/221 |
| 2,953,243 A | 9/1960 | Roehr | 206/43 |
| 3,021,942 A | 2/1962 | Hamilton | 206/43 |
| 3,073,307 A | 1/1963 | Stevens | 128/221 |
| 3,074,542 A | 1/1963 | Myerson et al. | 206/43 |
| 3,255,873 A | 6/1966 | Speelman | 206/56 |
| 3,294,231 A | 12/1966 | Vanderbeck | 206/63 |
| 3,323,523 A | 6/1967 | Scislowicz et al. | 128/214 |
| 3,329,146 A | 7/1967 | Waldman, Jr. | 128/221 |
| 3,333,682 A | 8/1967 | Burke | 206/43 |
| 3,367,488 A | 2/1968 | Hamilton | 206/63 |
| 3,485,239 A | 12/1969 | Vanderbeck | 128/218 |
| 3,537,452 A | 11/1970 | Wilks | 128/214 |
| 3,587,575 A | 6/1971 | Lichtenstein | 128/215 |
| 3,610,240 A | 10/1971 | Harautuneian | 128/214 |
| 3,658,061 A | 4/1972 | Hall | 128/214 |
| 3,828,775 A | 8/1974 | Armel | 128/218 |
| 3,840,008 A | 10/1974 | Noiles | 128/221 |
| 3,890,971 A | 6/1975 | Leeson et al. | 128/218 |

(List continued on next page.)

FOREIGN PATENT DOCUMENTS

| | | | | |
|---|---|---|---|---|
| EP | 0 344 606 A2 | 12/1989 | | A61M/5/32 |
| EP | 0 457 477 B1 | 11/1991 | | A61B/5/14 |
| EP | 0 485 345 B1 | 5/1992 | | A61M/5/32 |
| EP | 0 533 308 A1 | 3/1993 | | B41F/31/04 |
| EP | 0 585 391 B1 | 3/1994 | | A61M/5/32 |
| EP | 0 597 857 B1 | 5/1994 | | A61M/5/28 |
| EP | 0 603 365 B1 | 6/1994 | | A61M/5/32 |

(List continued on next page.)

*Primary Examiner*—Manuel Mendez
(74) *Attorney, Agent, or Firm*—Mark S. Leonardo; Peter B. Sorell; Brown Rudnick Berlack Israels LLP

(57) ABSTRACT

A safety shield for a medical needle device which is affixed to the medical needle device to thereby selectively provide protection for an associated medical needle with a sharpened distal tip. The safety shield may be so affixed with little or no changes in design to the medical needle device, and, importantly, after assembly of the device. The safety shield is foldable, comprising two hinged, elongated segments which are foldably compacted to provide ready access to the medical needle in a medical procedure, and unfoldable to provide a safety sheath for the needle. A free distal end of the safety shield permits the safety shield to be affixed to the medical needle device at the completion of device assembly, substantially independent of needle cover design and configuration. In an exemplary embodiment, a spur on a distal end of a proximal segment of a safety sheath is disposed to force a distal segment of the safety sheath securely against the needle when the safety shield is unfolded and displaced to assure covering safety of the needle when latched.

15 Claims, 9 Drawing Sheets

U.S. PATENT DOCUMENTS

| | | | |
|---|---|---|---|
| 3,904,033 A | 9/1975 | Haerr | 206/349 |
| 3,934,722 A | 1/1976 | Goldberg | 206/365 |
| 3,968,876 A | 7/1976 | Brookfield | 206/365 |
| 4,040,419 A | 8/1977 | Goldman | 128/215 |
| 4,106,621 A | 8/1978 | Sorenson | 206/365 |
| 4,113,090 A | 9/1978 | Carstens | 206/365 |
| 4,139,009 A | 2/1979 | Alvarez | 128/218 |
| 4,175,008 A | 11/1979 | White | 435/295 |
| 4,270,536 A | 6/1981 | Lemelson | 128/218 |
| 4,300,678 A | 11/1981 | Gyure et al. | 206/364 |
| 4,375,849 A | 3/1983 | Hanifl | 206/366 |
| 4,430,082 A | 2/1984 | Schwabacher | 604/263 |
| 4,592,744 A | 6/1986 | Jagger et al. | 604/192 |
| 4,634,428 A | 1/1987 | Cuu | 604/110 |
| 4,643,722 A | 2/1987 | Smith, Jr. | 604/192 |
| 4,659,330 A | 4/1987 | Nelson et al. | 604/192 |
| 4,664,259 A | 5/1987 | Landis | 206/365 |
| 4,664,654 A | 5/1987 | Strauss | 604/198 |
| 4,681,567 A | 7/1987 | Masters et al. | 604/198 |
| 4,695,274 A | 9/1987 | Fox | 604/198 |
| 4,702,738 A | 10/1987 | Spencer | 604/198 |
| 4,723,943 A | 2/1988 | Spencer | 604/198 |
| 4,728,320 A | 3/1988 | Chen | 604/110 |
| 4,728,321 A | 3/1988 | Chen | 604/110 |
| 4,731,059 A | 3/1988 | Wanderer et al. | 604/192 |
| 4,735,311 A | 4/1988 | Lowe et al. | 206/365 |
| 4,735,618 A | 4/1988 | Hagen | 604/192 |
| 4,737,144 A | 4/1988 | Choksi | 604/198 |
| 4,738,663 A | 4/1988 | Bogan | 604/198 |
| 4,743,233 A | 5/1988 | Schneider | 604/192 |
| 4,747,836 A | 5/1988 | Luther | 604/198 |
| 4,747,837 A | 5/1988 | Hauck | 604/198 |
| 4,772,272 A | 9/1988 | McFarland | 604/198 |
| 4,778,453 A | 10/1988 | Lopez | 604/110 |
| 4,781,697 A | 11/1988 | Slaughter | 604/192 |
| 4,782,841 A | 11/1988 | Lopez | 128/164 |
| 4,790,828 A | 12/1988 | Dombrowski et al. | 604/198 |
| 4,795,432 A | 1/1989 | Karczmer | 604/110 |
| 4,795,443 A | 1/1989 | Permenter et al. | 604/198 |
| 4,801,295 A | 1/1989 | Spencer | 604/198 |
| 4,804,372 A | 2/1989 | Laico et al. | 604/198 |
| 4,813,426 A | 3/1989 | Haber et al. | 128/763 |
| 4,816,022 A | 3/1989 | Poncy | 604/198 |
| 4,816,024 A | 3/1989 | Sitar et al. | 604/192 |
| 4,819,659 A | 4/1989 | Sitar | 128/764 |
| 4,820,277 A | 4/1989 | Norelli | 604/192 |
| 4,826,490 A | 5/1989 | Byrne et al. | 604/198 |
| 4,826,491 A | 5/1989 | Schramm | 604/198 |
| 4,838,871 A | 6/1989 | Luther | 604/192 |
| 4,840,619 A | 6/1989 | Hughes | 604/187 |
| 4,842,587 A | 6/1989 | Poncy | 604/198 |
| 4,846,796 A | 7/1989 | Carrell et al. | 604/110 |
| 4,846,811 A | 7/1989 | Vanderhoof | 604/263 |
| 4,850,968 A | 7/1989 | Romano | 604/110 |
| 4,850,976 A | 7/1989 | Heinrich et al. | 604/192 |
| 4,850,977 A | 7/1989 | Bayless | 604/198 |
| 4,850,978 A | 7/1989 | Dudar et al. | 604/201 |
| 4,850,994 A | 7/1989 | Zerbst et al. | 604/198 |
| 4,850,996 A | 7/1989 | Cree | 604/198 |
| 4,858,607 A | 8/1989 | Jordan et al. | 128/314 |
| 4,863,434 A | 9/1989 | Bayless | 604/198 |
| 4,863,435 A | 9/1989 | Sturman et al. | 604/198 |
| 4,863,436 A | 9/1989 | Glick | 604/110 |
| 4,867,172 A | 9/1989 | Haber et al. | 128/763 |
| 4,867,746 A | 9/1989 | Dufresne | 604/192 |
| 4,872,552 A | 10/1989 | Unger | 206/365 |
| 4,874,382 A | 10/1989 | Lindemann et al. | 604/195 |
| 4,874,383 A | 10/1989 | McNaughton | 604/198 |
| 4,874,384 A | 10/1989 | Nunez | 604/198 |
| 4,883,469 A | 11/1989 | Glazier | 604/192 |
| 4,886,503 A | 12/1989 | Miller | 604/192 |
| 4,887,998 A | 12/1989 | Martin et al. | 604/110 |
| 4,888,001 A | 12/1989 | Schoenberg | 604/162 |
| 4,892,107 A | 1/1990 | Haber | 128/763 |
| 4,892,521 A | 1/1990 | Laico et al. | 604/192 |
| 4,898,589 A | 2/1990 | Dolgin et al. | 604/198 |
| 4,900,309 A | 2/1990 | Netherton et al. | 604/192 |
| 4,904,244 A | 2/1990 | Harsh et al. | 604/187 |
| 4,911,694 A | 3/1990 | Dolan | 604/198 |
| 4,911,706 A | 3/1990 | Levitt | 604/198 |
| 4,927,018 A | 5/1990 | Yang et al. | 206/365 |
| 4,929,241 A | 5/1990 | Kulli | 604/263 |
| 4,935,012 A | 6/1990 | Magre et al. | 604/192 |
| 4,935,013 A | 6/1990 | Haber et al. | 604/192 |
| 4,936,830 A | 6/1990 | Verlier | 604/110 |
| 4,944,397 A | 7/1990 | Miller | 206/365 |
| 4,944,731 A | 7/1990 | Cole | 604/192 |
| 4,950,249 A | 8/1990 | Jagger et al. | 604/192 |
| 4,950,250 A | 8/1990 | Haber et al. | 604/192 |
| 4,978,344 A | 12/1990 | Dombrowski et al. | 604/198 |
| 4,982,842 A | 1/1991 | Hollister | 206/365 |
| 4,985,021 A | 1/1991 | Straw et al. | 604/198 |
| 4,994,041 A | 2/1991 | Dombrowski et al. | 604/164 |
| 5,000,744 A | 3/1991 | Hoffman et al. | 604/232 |
| 5,015,240 A | 5/1991 | Soproni et al. | 604/192 |
| 5,057,089 A | 10/1991 | Greco | 604/198 |
| 5,059,180 A | 10/1991 | McLees | 604/110 |
| 5,092,851 A | 3/1992 | Ragner | 604/192 |
| 5,108,379 A | 4/1992 | Dolgin et al. | 604/198 |
| RE34,045 E | 8/1992 | McFarland | 604/198 |
| 5,135,509 A | 8/1992 | Olliffe | 604/192 |
| 5,139,489 A | 8/1992 | Hollister | 604/192 |
| 5,147,303 A | 9/1992 | Martin | 604/110 |
| 5,154,285 A | 10/1992 | Hollister | 206/365 |
| 5,176,655 A | 1/1993 | McCormick et al. | 604/198 |
| 5,176,656 A | 1/1993 | Bayless | 604/198 |
| 5,193,552 A | 3/1993 | Columbus et al. | 128/760 |
| 5,195,983 A | 3/1993 | Boese | 604/192 |
| 5,209,739 A | 5/1993 | Talalay | 604/195 |
| 5,232,454 A | 8/1993 | Hollister | 604/192 |
| 5,232,455 A | 8/1993 | Hollister | 604/192 |
| 5,242,417 A | 9/1993 | Paudler | 604/192 |
| 5,242,418 A | 9/1993 | Weinstein | 604/192 |
| 5,246,427 A | 9/1993 | Sturman et al. | 604/192 |
| 5,246,428 A | 9/1993 | Falknor | 604/198 |
| 5,250,031 A | 10/1993 | Kaplan et al. | 604/110 |
| 5,254,099 A | 10/1993 | Kuracina et al. | 604/198 |
| 5,256,152 A | 10/1993 | Marks | 604/198 |
| 5,256,153 A | 10/1993 | Hake | 604/198 |
| 5,277,311 A | 1/1994 | Hollister | 206/365 |
| 5,290,255 A | 3/1994 | Vallelunga et al. | 604/197 |
| 5,304,137 A | 4/1994 | Fluke | 604/110 |
| 5,312,369 A | 5/1994 | Arcusin et al. | 604/192 |
| 5,334,158 A | 8/1994 | McLees | 604/110 |
| 5,348,544 A * | 9/1994 | Sweeney et al. | 604/192 |
| 5,356,392 A | 10/1994 | Firth et al. | 604/198 |
| 5,403,283 A | 4/1995 | Luther | 604/164 |
| 5,403,286 A | 4/1995 | Lockwood, Jr. | 604/110 |
| 5,407,436 A | 4/1995 | Toft et al. | 604/195 |
| 5,411,492 A | 5/1995 | Sturman et al. | 604/263 |
| 5,423,765 A | 6/1995 | Hollister | 604/192 |
| 5,423,766 A | 6/1995 | Di Cesare | 604/192 |
| 5,425,720 A | 6/1995 | Rogalsky et al. | 604/198 |
| 5,447,501 A | 9/1995 | Karlsson et al. | 604/198 |
| 5,466,223 A | 11/1995 | Bressler et al. | 604/110 |
| 5,480,385 A | 1/1996 | Thorne et al. | 604/110 |
| 5,487,733 A | 1/1996 | Caizza et al. | 604/110 |
| 5,487,734 A | 1/1996 | Thorne et al. | 604/195 |
| 5,498,243 A | 3/1996 | Vallelunga et al. | 604/197 |
| 5,531,694 A | 7/1996 | Clemens et al. | 604/110 |
| 5,533,980 A | 7/1996 | Sweeney et al. | 604/192 |

| | | | |
|---|---|---|---|
| 5,538,508 A | 7/1996 | Steyn | 604/192 |
| 5,542,927 A | 8/1996 | Thorne et al. | 604/110 |
| 5,549,568 A | 8/1996 | Shields | 604/192 |
| 5,549,570 A | 8/1996 | Rogalsky | 604/198 |
| 5,549,708 A | 8/1996 | Thorne et al. | 604/110 |
| 5,562,629 A | 10/1996 | Haughton et al. | 604/158 |
| 5,562,631 A | 10/1996 | Bogert | 604/164 |
| 5,573,510 A | 11/1996 | Isaacson | 604/158 |
| 5,584,816 A | 12/1996 | Gyure et al. | 604/192 |
| 5,584,818 A | 12/1996 | Morrison | 604/197 |
| 5,643,220 A | 7/1997 | Cosme | 604/192 |
| 5,672,161 A | 9/1997 | Allen et al. | 604/263 |
| 5,695,474 A | 12/1997 | Daugherty | 604/162 |
| 5,695,477 A | 12/1997 | Sfikas | 604/241 |
| 5,700,249 A | 12/1997 | Jenkins | 604/263 |
| 5,735,827 A | 4/1998 | Adwers et al. | 604/263 |
| 5,738,665 A | 4/1998 | Caizza et al. | 604/263 |
| 5,746,718 A | 5/1998 | Steyn | 604/192 |
| 5,746,726 A | 5/1998 | Sweeney et al. | 604/263 |
| 5,755,699 A | 5/1998 | Blecher et al. | 604/198 |
| 5,814,018 A | 9/1998 | Elson et al. | 604/110 |
| 5,823,997 A | 10/1998 | Thorne | 604/110 |
| 5,843,041 A | 12/1998 | Hake et al. | 604/198 |
| 5,910,130 A * | 6/1999 | Caizza et al. | 604/110 |
| 5,919,168 A | 7/1999 | Wheeler | 604/198 |
| 5,925,020 A | 7/1999 | Nestell | 604/198 |
| 5,957,892 A | 9/1999 | Thorne | 604/162 |
| 5,980,488 A | 11/1999 | Thorne | 604/110 |
| 6,015,397 A | 1/2000 | Elson et al. | 604/192 |
| 6,036,675 A | 3/2000 | Thorne et al. | 604/232 |
| 6,149,629 A | 11/2000 | Wilson et al. | 604/198 |
| RE37,110 E | 3/2001 | Hollister | 206/365 |
| 6,224,576 B1 * | 5/2001 | Thorne et al. | 604/198 |
| RE37,252 E | 7/2001 | Hollister | 206/364 |
| 6,254,575 B1 * | 7/2001 | Thorne, Jr. et al. | 604/198 |
| 6,280,420 B1 * | 8/2001 | Ferguson et al. | 604/198 |
| 6,334,857 B1 | 1/2002 | Hollister et al. | |

FOREIGN PATENT DOCUMENTS

| | | | |
|---|---|---|---|
| EP | 0 626 924 B1 | 12/1994 | A61M/5/32 |
| EP | 0 654 281 B1 | 5/1995 | A61M/5/32 |
| EP | 0 705 613 B1 | 4/1996 | A61M/5/31 |
| EP | 0 815 888 A2 | 1/1998 | A61M/5/00 |
| EP | 0 815 890 A2 | 1/1998 | A61M/5/00 |
| EP | 0 819 441 A1 | 1/1998 | A61M/5/32 |
| EP | 0 832 659 A2 | 4/1998 | A61M/5/00 |
| EP | 0 832 660 A2 | 4/1998 | A61M/5/32 |
| GB | 1233302 | 5/1971 | A61B/17/06 |
| GB | 2 283 429 A | 12/1997 | A61M/5/32 |
| JP | 10-76007 | 3/1998 | A61M/5/32 |
| JP | 10-127765 | 5/1998 | A61M/5/178 |
| WO | WO 87/07162 | 12/1987 | A61M/5/32 |
| WO | WO 89/07955 | 9/1989 | A61M/5/32 |
| WO | WO 94/19036 | 9/1994 | A61M/5/32 |
| WO | WO 98/07463 | 2/1998 | A61M/5/32 |
| WO | WO 98/10816 | 3/1998 | A61M/5/32 |
| WO | WO 98/11928 | 3/1998 | A61M/5/00 |
| WO | WO 98/12081 A1 | 4/1998 | B60R/21/28 |
| WO | WO 00/16832 | 3/2000 | A61M/5/32 |
| WO | WO 01/32241 A1 | 5/2001 | A61M/5/00 |
| WO | WO 01/32244 A1 | 5/2001 | A61M/5/32 |

* cited by examiner

MEDICAL NEEDLE SAFETY APPARATUS AND METHODS

FIELD OF INVENTION

This invention relates generally to safety devices for hollow bore medical needles and particularly to medical syringe, butterfly and other hollow bore needle products and especially pre-filled syringes which employ protective needle sheaths for securely shielding sharp medical needle tips after being withdrawn from a patient and, still more particularly, to safety devices which can be affixed to a needle product at the end of a manufacturing cycle. This invention also particularly relates to sheaths or shrouds which are extended to a locked, needle-covering position after the needle is withdrawn from the patient.

PRIOR ART

Problems associated with inadvertent needle sticks are well known in the art of blood sampling, percutaneous medication injection and other medical procedures involving uses of medical needles. Ever increasing attention is being paid to needle stick problems due to the contemporary sensitivity of exposure to AIDS, Hepatitis and other serious blood-borne diseases.

Commonly, procedures involving removing a needle from a patient require a technician to use one hand to place pressure at the wound site where the needle is being withdrawn while removing the needle apparatus with the other hand. It is common practice for a tending technician to give higher priority to care for the wound than is given to disposal of a needle. In the case of commonly used, non-safety devices such priority either requires convenience of an available sharps container within ready reach or another means for safe disposal without leaving the patient's side. Providing adequate care is often compounded by patient condition and mental state (e.g. in burn units and psychiatric wards). Under such conditions, it is often difficult, if not impossible, to use appropriate procedures to properly dispose of a used, exposed needle while caring for a patient.

Widespread knowledge and history associated with needle care and disposal problems have resulted in conception and disclosure of a large number of devices each of which represents an attempt to provide not only a solution to the problem of needle sticks, but also a device which is commercially viable (i.e. cost and price competitive with currently used non-safety devices).

Examples of disclosures of safety devices which protect needles by moving a protective shield over a sharp end of a syringe or other hollow bore medical needle are found in U.S. Pat. No. 5,348,544, issued Sep. 20, 1994 to Sweeney et al. (Sweeney), U.S. Pat. No. 5,246,428 issued Sep. 21, 1993 to Donald W. Falknor (Falknor), U.S. Pat. No. 5,256,153 issued Oct. 26, 1993 to Lawrence W. Hake (Hake), U.S. Pat. Nos. 5,139,489 and 5,154,285, issued Aug. 18, 1992 and Oct. 13, 1992, respectively, to William H. Hollister (Hollister) and U.S. Pat. No. 5,823,997 issued Oct. 20, 1998 and U.S. Pat. No. 5,980,488 issued Nov. 9, 1999 to David L. Thorne (Thorne). There are many other examples of safety devices which retract needles into housings, however, this instant invention is more directly related to devices which extend a shield over a needle rather than to those which employ needle retraction.

Sweeney discloses a device comprising a guard which is manually, slidably movable along a needle canula from a position proximal to a user to a distal position where the needle tip is shielded. The device comprises a hinged arm which extends along the needle canula and which is moved distally to collapse upon itself to extend the guard over the tip. Access to the tip is taught to be denied by a metallic clip associated with the guard, although, if the guard is securely affixed along the needle, the Sweeney device may be provided without a metallic clip. An alternative embodiment is also disclosed by which the manual operation is augmented by a spring. A device based upon Sweeney is currently being distributed by Becton Dickinson and Company, Franklin Lakes, N.J. in which three separate parts (two injection molded and one metal clip) are used to mechanize the guard. Once the device is extended to shield a needle tip, it cannot be easily reset to recover use of the needle for a subsequent procedure. Also, the hinged arm requires activation in the region of the needle itself and comprises parts which are of a size which occasionally impedes a user's line of sight to insertion locations.

Falkner, and related disclosures, disclose devices comprising shields which are automatically releasible to extend distally from a user to cover a needle. The devices comprise latch mechanisms which are manually switched between unlatched and latched positions to free the needle for use and lock the shield over the needle, respectively. Of course, position of the latch mechanism provides a visual interpretation of the safety of the device (i.e. whether or not a latch is engaged), but that is the only safety mechanism and a "missed" indicator of latch mechanism position may be possible in stressful circumstances. When the latch mechanism is in the unlatched position, access to the needle is not only possible, but likely when the front of the device is impacted by a body part. In addition, the shield, though made of transparent material, covers a portion of an attached syringe body until fully extended and may make portions of volume measurement indicia on the syringe body difficult to read with accuracy when the syringe is being used in a titrating application.

Hake is representative of disclosure of devices comprising a manually slidable guard which is disposed over a syringe body during a medical procedure involving a medical syringe needle and manually, slidably moved distally into a needle guarding position usually at the end of the procedure. Commonly users of such devices complain of difficulty of seeing measurement indicia while the guard is disposed over the syringe body and of danger of inadvertent needle sticks while sliding the guard distally to cover the needle. As well, it is generally difficult to determine whether a guard is in a locked or unlocked state when it covers the needle, making an additional possibility of inadvertent needle stick.

Hollister discloses a needle protection device which may be used with a double-ended needle assembly or with a simpler single needle system. The protection device comprises a substantially rigid housing flexibly connected to a container (for a vacuum tube sampling system) or to a needle hub. To exercise the protection device, the rigid member is pivotally rotated into engagement with an exposed needle of the double-ended needle assembly and is securely affixed to the exposed needle. A major drawback of the needle protection device of Hollister is the size and position of the rigid housing. During use of a needle assembly or system in a medical procedure, length and position of the housing member is considered by some to be inconvenient. A second drawback is the requirement either for two handed operation to pivot the housing to engage the needle or for the requirement to find and use a stable support surface against which the housing is pressed while the needle is swung into engagement with the housing. In a currently marketed format, an integral container holder version of the device disclosed by Hollister comprises two injection molded parts which permit the housing to be rotated, as much as possible, out of the way during a medical procedure. Such a format requires five injection molded parts, including a disposable needle assembly.

Thorne discloses a needle sheath which folds about a medical needle to permit access to the needle in a medical procedure. The sheath is hingeably attached to a structure (e.g. a needle hub or phlebotomy barrel) at a point away from a sharpened needle tip which is later enclosed by the needle sheath to protect a user from a stick by the needle tip. At the end of the procedure, the sheath is unfolded and extended away from the structure in the direction of the needle tip to encase and thereby protect users from contact with the needle and its tip. To permit the sheath to unfold about the needle, each folded part of the sheath is serially constructed of a plurality of rigid segments. At least one segment comprises an orifice through which the needle passes and about which that segment rotates while the sheath is being extended. Each segment is connected to at least one other segment by a hinge, which is preferably a molded, living hinge, and comprises a channel into which the needle nests when the sheath is fully extended. At least one of the segments comprises a catch which securely captures the needle when it is disposed in the sheath. Once the sheath is extended and the needle so captured, the combination of sheath and needle form a substantially rigid member which shrouds the needle and its sharpened tip to provide safety from dangerous contact with the tip and needle.

While folded needle sheaths, such as those disclosed in Sweeney and Thorne have desirable features related to needle safety and simplicity of actuation, all known foldable needle sheaths have severe disadvantages when attempts are made to affix such sheaths to needle devices already assembled. Generally, needle covers affixed over related medical needles are made to conform to pre-existing needle hub geometry. The known foldable needle sheaths depend upon a structure which is disposed about the needle in one way or another, resulting in a design change to accommodate one of the known safety shields.

This is a serious concern when considering the vast investment commonly made in automated assembly equipment and the additional cost of remodeling such equipment to install a safety sheath assembly in the middle of an existing automated line. In some cases, devices as taught by Thorne have been configured to fit over a needle cover and thereby affixed at the end of an automated line, but a natural consequence of a device which employs a foldable sheath having parts which must be disposed about a needle is a sheath or shield which significantly increases the girth of the device in the area of the device needle hub (e.g. in the case of a syringe, in the area of the distal end of the syringe barrel).

Generally, other than acceptance of the type of operation offered by such devices, commercial viability is dependent upon manufacturing cost. Purchase decisions in the area in which these devices are used are very cost sensitive. If gains in either improvement in safety or in labor savings are not found to make a device sufficiently competitive with contemporary competitive items, those devices are usually not found to be commercially viable. This same cost sensitivity applies to cost of refurbishing an automated assembly line to accommodate a safety needle shield.

BRIEF SUMMARY AND OBJECTS OF THE INVENTION

In brief summary, the novel invention disclosed herein dramatically diminishes known major problems resulting from injury-related needle sticks which occur when needle tips are bared as medical needles are withdrawn from a patient at the end of a needle insertion procedure, but, perhaps more important to general patient welfare, these inventions provide opportunity for fabrication of a very low cost safety needle system. This opportunity is augmented by a further opportunity to affix a safety sheath assembly to a standard, completely assembled needle device at the end of an automated assembly line, requiring little or no changes to the device itself or to the automated assembly line, associated with manufacture and assembly of the device.

For purposes of this disclosure, a needle "shield" is defined to be apparatus which protectively covers a medical needle for safety. A "sheath" is a portion of a shield apparatus which encases or encloses the medical needle to serve as the critical element of the shield. An interlock is a combination of parts of a needle shield which act to urge displaced portions or members of a needle sheath into planar alignment relative to an associated medical needle and to achieve substantial rigidity of the portions or members thereby. As an example, an interlock may be associated with a first sheathing portion or member which is rotated and contacts a second sheathing portion to thereby cause the second sheathing portion or member to become rigidly affixed relative to the medical needle and first sheathing portion or member when the needle shield is unfolded and the shield is latched in a safety orientation relative to the medical needle. Also, for purposes of this disclosure, the term "spur" is defined to be an appendage distending from a one sheathing part to contact and urge a contacted portion of a second sheathing part in a direction of travel of the spur. Such a spur is thereby considered to be a part of an interlock.

It is a primary object to provide an unfoldable medical needle shield apparatus associated with a medical needle device which is folded into a compact state to permit access to a medical needle and an associated distally disposed sharpened tip for use in a medical procedure and unfolded and displaced about the medical needle to provide a protective safety sheath about at least the distally disposed sharpened tip of the medical needle, the shield apparatus comprising:

a shield connector assembly whereby the needle shield apparatus is securely affixed to the medical needle device;

a needle shield, hingeably affixed to the shield connector assembly, which provides the foldable portion of the apparatus, the shield comprising:

a proximally disposed substantially rigid, elongated first sheath member comprising a first end at which the shield is hingeably affixed to the connector assembly such that the proximal sheath member rotates in-line with the medical needle when the shield is unfolded and extended and a second end which is distally disposed relative to the first end when the shield is unfolded;

a substantially rigid, elongated second sheath member comprising a connected end hingeably affixed to the second end such that the second sheath member also rotates in-line with the medical needle when the shield is unfolded and an end free of connection to any other part when the shield is folded, the first sheathing member, in combination with the second sheathing member, comprising a length which extends along the length of the medical needle for safety when the shield is unfolded and at least the second sheath member being disposed about and sheathing the needle;

at least one latch associated with the shield by which the shield is unreleasibly latched to be securely affixed in place relative to the medical needle and associated sharpened tip when the shield is unfolded and disposed about the needle; and the second end, in combination with the connected end, further comprising an interlock by which the second sheath member is forced into alignment with the needle as the shield is unfolded and securely latched as a safety sheath about the medical needle.

It is a further object to provide a spur which acts to engage the interlock.

It is an object to provide a button on the first sheathing member which facilitates unfolding of the shield.

It is an object to provide a latch and catch associated with the shield connector assembly and elongated first sheath member, in combination, which securely retains the shield apparatus about the medical needle when the shield apparatus is unfolded and so disposed.

It is an object to provide structure associated with the medical needle shield apparatus which permits the medical needle shield apparatus to be affixed to the medical needle device without impacting operational removal of a cover disposed about the medical needle and associated tip during storage and transport of the medical needle device before use.

It is an object to provide a second sheath member having a groove in the connection free end which acts as a track within which the medical needle glides as the needle shield is unfolded.

It is an object to provide a combination of sheath members whereby the second sheath member is longer than the first sheathing member to effectively impede binding as the needle shield unfolds.

It is an important object to provide a method for enclosing a sharpened medical needle in a safety shield comprising the steps of:

providing a medical needle device comprising a hollow bore cannula securely affixed in a hub and aseptically covered by a needle cover, the cannula having at least one sharpened tip to form the medical needle, and a safety shield assembly which is hingeably joined to the hub after assembly of the medical needle device, the safety shield assembly comprising an elongated, foldable sheath which comprises a pair of serially interconnected substantially rigid segments each of which being interconnected to the adjacent segment by an intersegment hinge, a first segment comprising a free end, which is unattached to any other portion of the part, and a second segment, in combination with the first segment, providing an interlock which acts about the intersegment hinge to force the segment with the free end against the needle as the sheath is unfolded, and comprising a channel in which at least a part of the cannula is disposed when the sheath is linearly extended, the sheath and the hinges being disposed to permit folding of the sheath about the hub in a first state to permit usable access to the medical needle in a medical procedure and unfolding and extending of the sheath to a substantially planar disposition along the cannula whereat the cannula is disposed along the channel, the sheath further comprising at least one latching member which catches and securely affixes the sheath in relation to the cannula, the sheath and cannula, in combination, thereby forming a substantially rigid body which protectively encloses the sharpened tip and denies access thereto;

assembling the medical needle device without the safety shield assembly;

affixing the safety shield assembly to the medical needle device to form a safety medical needle device;

transporting and storing the safety medical needle device prior to use;

removing the safety medical needle device from storage preparatory for use;

removing the needle cover from the cannula and folded sheath, leaving the shield assembly in a compact, stable, but releasible, state such that the needle tip is accessible for a medical procedure; and at the end of the medical procedure, displacing a proximal segment of the sheath to unfold segments of the sheath, forcing the interlock to engage the intersegment hinge until the at least one latching member is engaged to form the substantially rigid body and thereby protectively enclose and deny access to the sharpened tip.

It is another important object to provide an unfoldable safety medical needle apparatus comprising:

a medical needle having a sharpened tip disposed on a distal end;

a removable needle cover which, in cooperation with a hub for the medical needle, is disposed about the medical needle to provide a fluid flow resistant seal for antiseptic purposes, the cover being removed for access to the medical needle for use in a medical procedure;

a safety shield assembly comprising:

a safety sheath which is folded and compacted to permit the removable needle cover to be so disposed about the medical needle and to also permit access to the medical needle and associated distally disposed sharpened tip for use in a medical procedure and unfolded to be displaced about the medical needle to provide a protective safety sheath about at least the distally disposed sharpened tip;

the medical needle hub in which a proximal end of the medical needle is affixed;

structure associated with the medical needle hub comprising connective geometry by which the needle cover is releasibly affixed to the medical needle hub and by which a proximally disposed fluid vessel is connected to the medical needle hub thereby providing fluid access between the vessel and the medical needle;

a sheath connector assembly whereby the safety sheath is firmly affixed to the structure;

the foldable needle sheath hingeably affixed to the sheath connector assembly, the sheath comprising:

a proximally disposed substantially rigid, elongated first sheath member comprising a first end at which the sheath is hingeably affixed to the connector assembly such that the proximal sheath member rotates in-line with the medical needle when the sheath is unfolded and extended and a second end which is distally disposed relative to the first end when the sheath is unfolded;

a substantially rigid, elongated second sheath member comprising a connected end hingeably affixed to the second end such that the second sheath member also rotates in-line with the medical needle when the sheath is unfolded and an end free of connection to any other part, the first sheath member in combination with the second sheath member comprising a length which extends completely along the medical needle such that at least the second sheath member provides a sheath which shields at least the sharpened tip for safety when the sheath is unfolded;

at least one latch associated with the shield by which the sheath is unreleasibly latched to be securely affixed in place relative to the medical needle and associated sharpened tip when the sheath is unfolded about the needle; and the second end, in combination with the connected end, further forming an interlock by which the second sheath member is forced into alignment with the needle to be securely latched as a safety shield about the medical needle as the sheath is unfolded.

These and other objects and features of the present invention will be apparent from the detailed description taken with reference to accompanying drawings.

DETAILED DESCRIPTION OF THE ILLUSTRATED EMBODIMENTS

In this description, unless a specific object is otherwise specified, the term "proximal" is used to indicate the segment of a device normally closest to a user (e.g. a clinician or technician who is treating a patient). In like manner, the term "distal" refers to the other (away from the user) end. Reference is now made to the embodiments illustrated in FIGS. 1–5, including FIGS. 1A–4A, wherein like numerals are used to designate like parts throughout.

Figure 1:
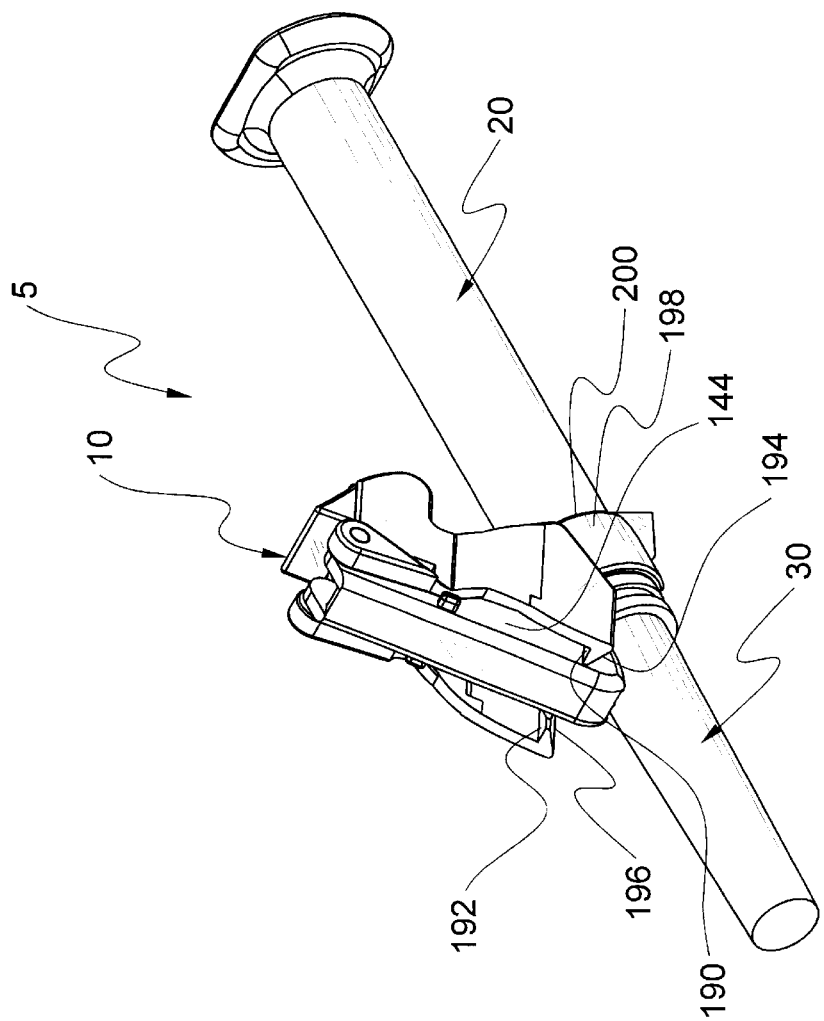
FIG. 1 is a perspective of a device having a safety shield affixed to a syringe barrel with a needle cover disposed about an unseen medical needle affixed to the syringe barrel beneath the needle cover.

Reference is now made to FIG. 1 wherein a medical apparatus, generally designated by the numeral 5, comprises a safety needle shield 10, made according to the instant invention, is affixed to a syringe barrel 20 and a needle cover 30 is disposed about a medical needle (not seen in FIG. 1). Generally, needle cover 30 is disposed about the medical needle for storage and transport prior to use. Such needle covers are in common commercial use world wide.

Figure 2:
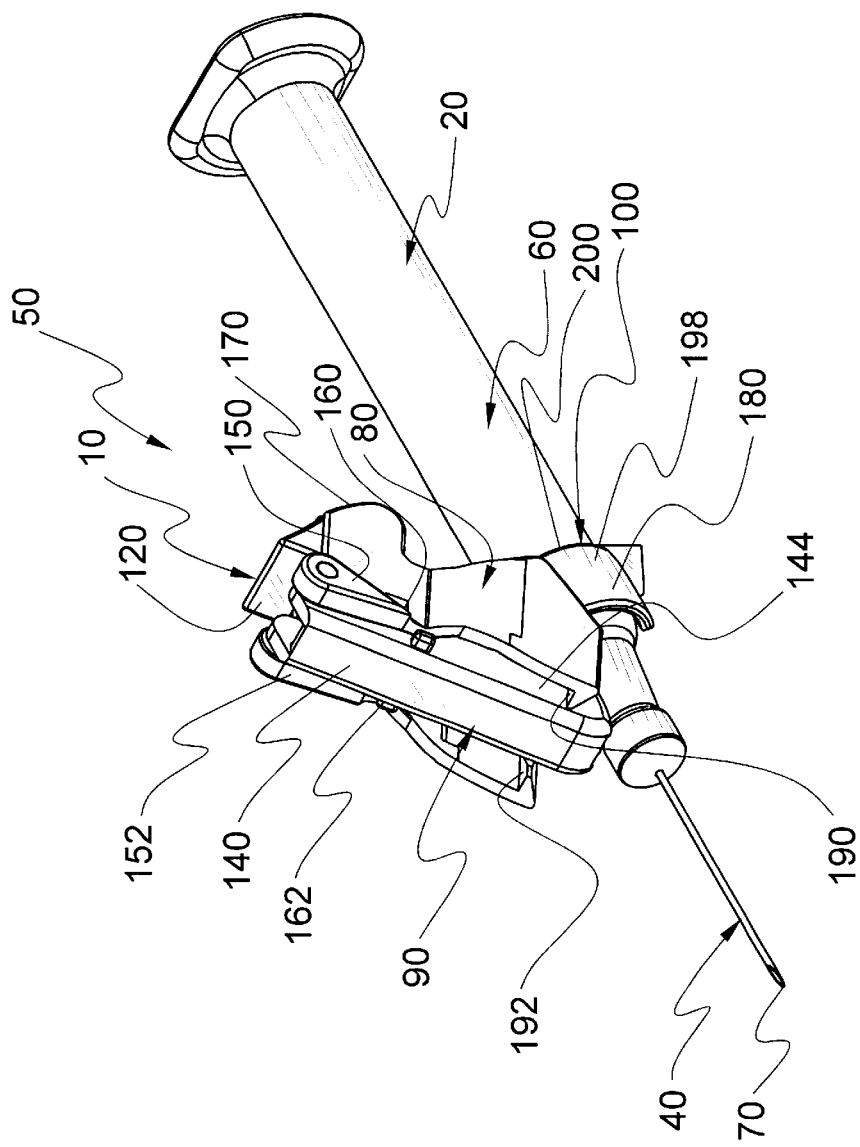
FIG. 2 is a perspective of the safety shield and syringe barrel of the device seen in FIG. 1 with the cover removed for access to the medical needle.

As seen in FIG. 2, needle cover 30 is removed to bare a medical needle 40 for use. So configured, the remaining device of apparatus 5, comprising shield 10, syringe barrel 20 and medical needle 40, as seen in FIG. 2, is referenced as device 50.

Figure 1A:
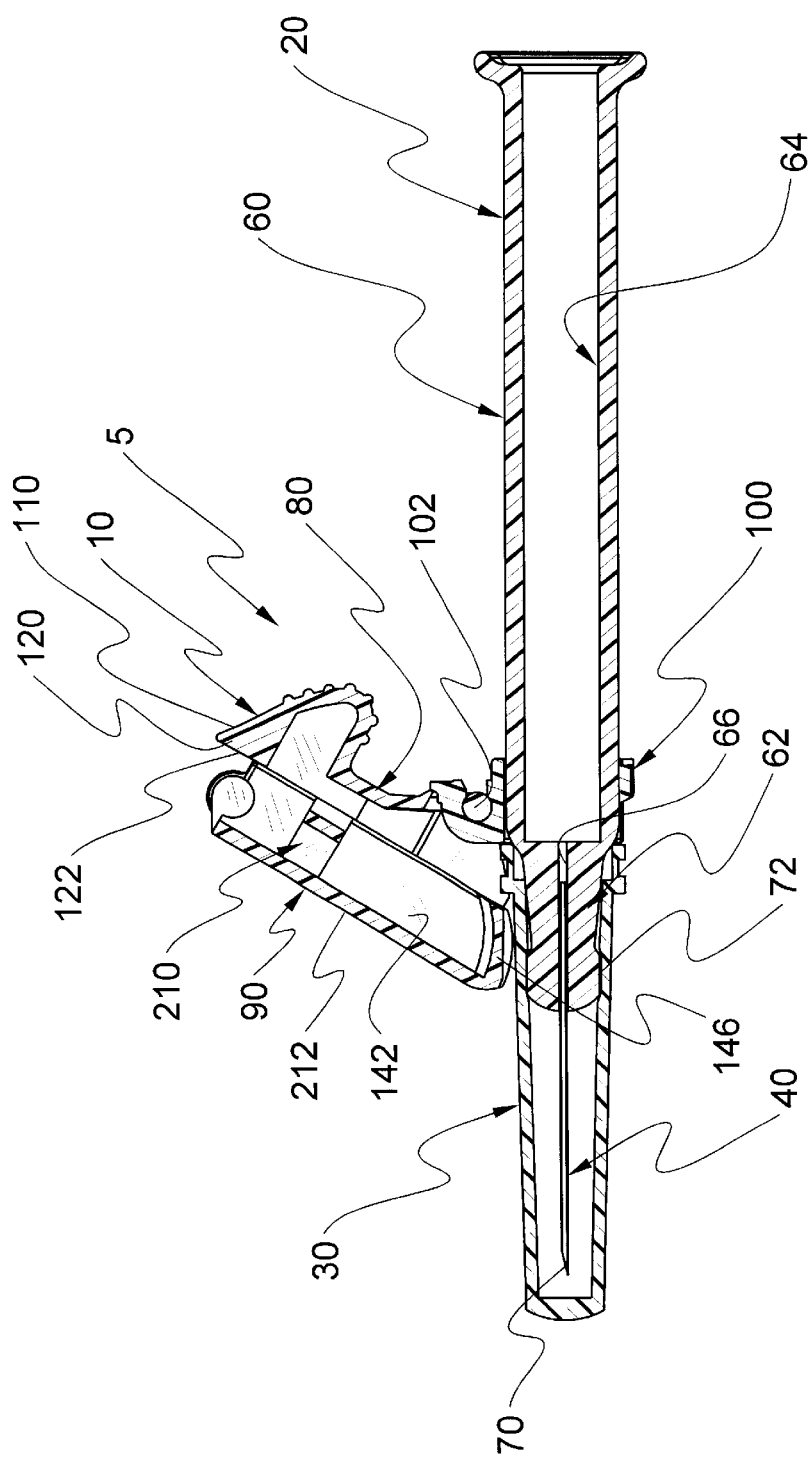
FIG. 1A is a cross section of a lateral elevation of the device as seen in FIG. 1.
Figure 2A:
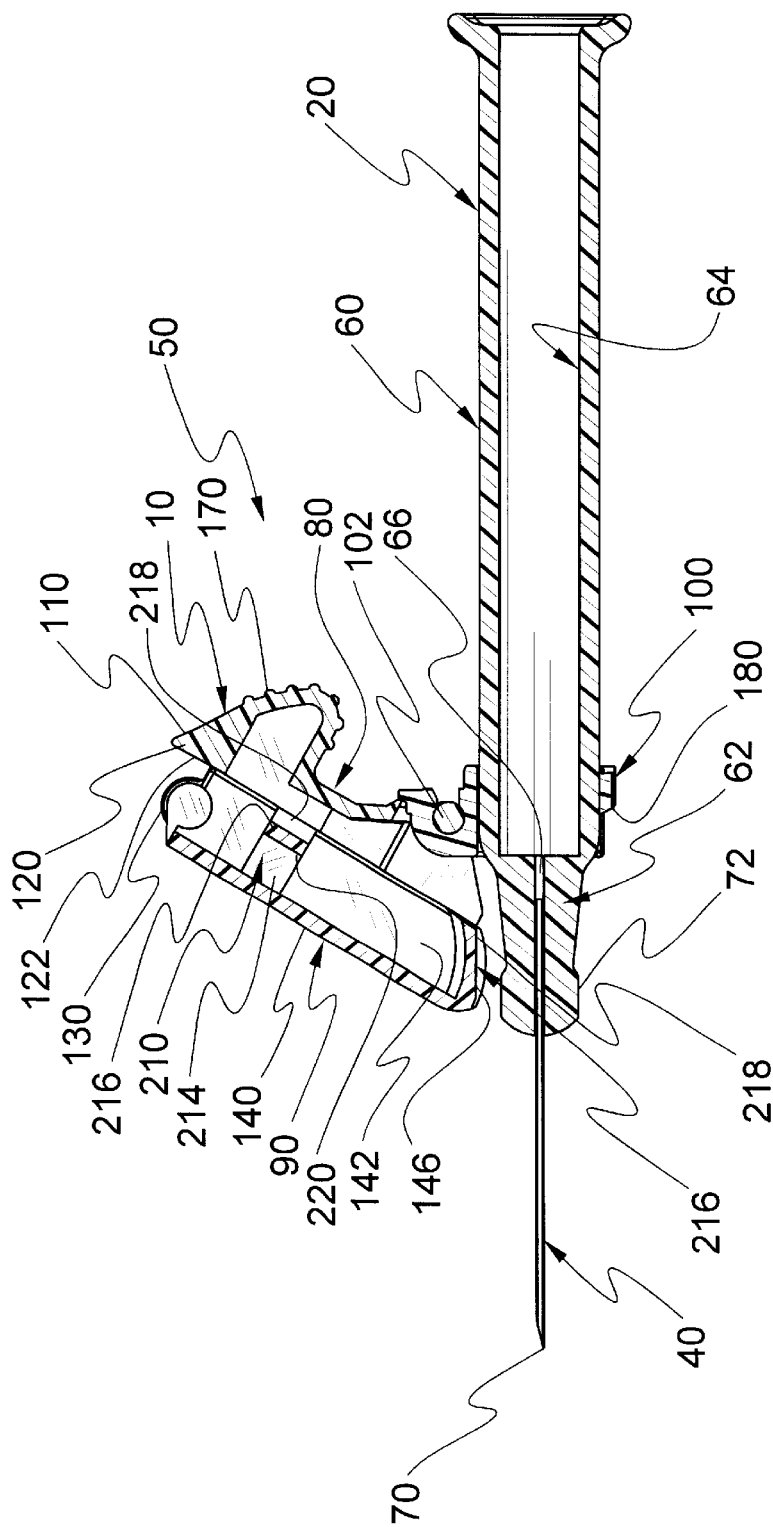
FIG. 2A is a cross section of a lateral elevation of the device as seen in FIG. 2.

As seen in FIGS. 1A and 2A, syringe barrel 20 has an elongated portion 60 distally disposed to a cover 30 connecting portion 62. Portion 60 has a cylindrical hollow interior surface 64 along which a syringe plunger (not shown as such plungers are commonly available in the syringe art) is urged to encourage fluid flow through medical needle 40.

Cover connecting portion 62 has axially disposed orifice 66 in which medical needle 40 is securely affixed to assure fluid flow communication through medical needle 40 into barrel portion 60. Of course, for percutaneous use, medical needle 40 has a distally disposed sharpened tip 70. Further portion 62 has an exteriorly disposed surface 72 which is sized and configured to releasibly affix cover 30 to device 50 to form apparatus 5. Such surface 72 design and cover 30 attachment is well known in syringe manufacture art. It is of particular importance to note that, while special barrel components may be made for device 50 within the scope of the instant invention disclosed herein, device 50 is readily adaptable to existing syringe assemblies having predetermined barrel configurations and cover connections. Also, as will be apparent from disclosure which follows herein, shield 10 is adaptable to a wide range of needle sizes and lengths.

Also, as seen in FIGS. 1A and 2A, shield 10 has a proximally disposed, substantially rigid, elongated sheath member 80 and a substantially rigid, elongated, more distally disposed sheath member 90. Sheath member 80 is hingeably affixed to a connector assembly 100 and which is securely affixed to barrel portion 60. Note that a hinge 102 is shown as a pin hinge in the figures, but may be formed as a living hinge when connector assembly 100 and sheath member 80 are molded as a single injection molded part. Such combining of hingeably associated injection molded parts is well known in the medical device molding art.

It should be noted that barrel parts may be molded from glass or synthetic resinous material. Material selection decisions are based upon ultimate projected use of such a syringe and, since shield 10 and connector assembly 100 may be affixed after manufacture to syringes which are made by an original device manufacturer, no specification for such decisions are required to be provided herein. However, care should be taken in design of modes of attachment of connector assembly 100 to each different barrel portion 60 (or other attachable portion of a given barrel 20) to assure device 50 remains securely affixed to each barrel 60.

At a superiorly disposed end 110 (as seen in FIGS. 1A and 2A) of sheath member 80, sheath member 80 is fitted with an outwardly distending spur 120. In particular, spur 120 has a distally facing surface 122, the purpose for which is disclosed in detail hereafter. Associated with surface 122 is a hinge part 130 which hingeably affixes sheath member 80 to sheath member 90.

Generally, inferiorly disposed to hinge part 130, sheath member 90 has a top side 140 and a pair of laterally disposed sides 142 and 144 (note that the only side seen in FIGS. 1A and 2A is side 142 due to segmentation. See FIG. 1 to view side 144). Each side 140, 142 and 144 extend from hinge part 130 to be commonly truncated by a closed, free end 146. Note that end 146 need not be closed, although it is preferred that end 146 be closed for some assurance of greater safety.

Shield 10 is deployed in a folded state as seen in FIGS. 2 and 2A to provide user access to medical needle 40 in a medical procedure. Of course, it is preferred that shield 10 be stable while in the folded state. For this reason a pair of releasible latches 150 and 152 and a pair of associated catches 160 and 162 (as seen in FIG. 2) are disposed on exterior sides of sheath member 90 and sheath member 80, respectively. These latches and catches are released by forced rotation of sheath member 80 toward sharpened needle end 70.

To facilitate such rotation of sheath member 80, a protrusion 170(i.e. a button 170) is disposed on a proximal side of sheath member 80. It should be noted that all hinges are disposed to assure that, as shield 10 is displaced from the folded state, sheath members 80 and 90 rotate along a line parallel with the long axis of needle 40.

As seen in FIG. 2, connector assembly 100 has a collar 180 by which connector assembly 100 is securely affixed to barrel portion 60. Collar 180 is sized to fit snugly about barrel portion 60 and may be further secured by adhesive. Adhesives which can be used for such purposes are well known to those who have expertise in the medical device assembly art. It may be noted that connector assembly 100 may not necessarily be affixed to barrel portion 60, but may be attached to or even injection molded as an integral part to connecting portion 62, which acts as a hub for needle 40. However, if it is desired to have needle shield 10 affixed after assembly of medical needle 40 to barrel 20, or especially after cover 30 has been placed about needle 40, shield 10 is preferably affixed by a collar, like collar 180, to barrel portion 60.

Figure 3:
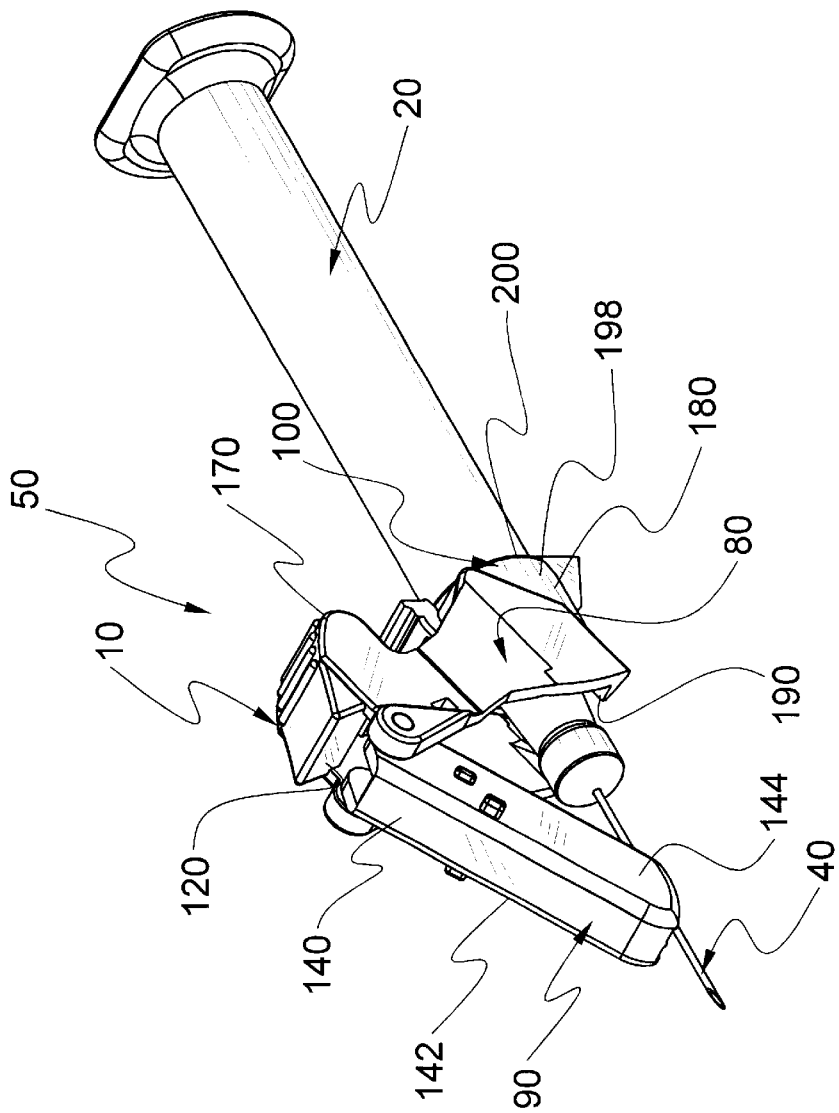
FIG. 3 is a perspective of the device seen in FIG. 2 with the safety shield partially unfolded above the medical needle.

As clearly seen in FIGS. 1,2 and 3, proximally disposed sheath member 80 has a pair of initially inferiorly disposed, inwardly directed, triangularly shaped wings 190 and 192. Note that, on an inferior side (numbered 194 and 196, respectively), each wing 190 and 192 is slanted for ease of passage about collar 180 as sheath member 80 is rotated about hinge 102 (see FIG. 2A) while shield 10 is unfolded. Further, an outer, lateral surface 198 of collar 180 is displaced outward from barrel 20 and ends abruptly on a proximal edge 200. Thus, as sheath member 80 is rotated substantially to the same plane as needle 40, each wing 190 and 192 is sized and shaped to rotate about collar 180 and latch unreleasibly upon a catch formed by edge 200. In this manner, when needle 40 is sheathed by members 80 and 90 there is a catch in place to assure needle tip 70 is unreleasibly enclosed by sheath member 90 for safety, as seen in FIGS. 4 and 4A.

It may also be noted in FIG. 2A, that a second latch part 210 is disposed in sheath member 90. Latch part 210 is affixed to superior side 140 and offset from the long axis of needle 40. Latch part 210 has an elongated side member 214 which extends inwardly away from side 140 to abruptly end at a clip 216. Clip 216 extends transversely to cross the path of needle 40 as shield 10 is unfolded and has a sloping inferior surface 218 (as seen in FIG. 4A) which allows clip 216 to proceed past needle 40, when relieved by bending of elongated member 214, as sheath member 90 is unfolded about needle 40. Further clip 216 has a superior surface 220 (also as seen in FIG. 4A) which latches against needle 40 to retard sheath member 90 from being released from enclosing needle 40 and needle tip 70 once shield 10 is unfolded. It may be noted that latch part 210 may be considered to be redundant when wings 190 and 192 are disposed to be latched upon proximal edge 200 of collar 180, as seen in part in FIG. 4A. However, for safety systems, redundancy, if achieved for little or no additional cost is highly desired and in this case may be preferred.

Figure 4:
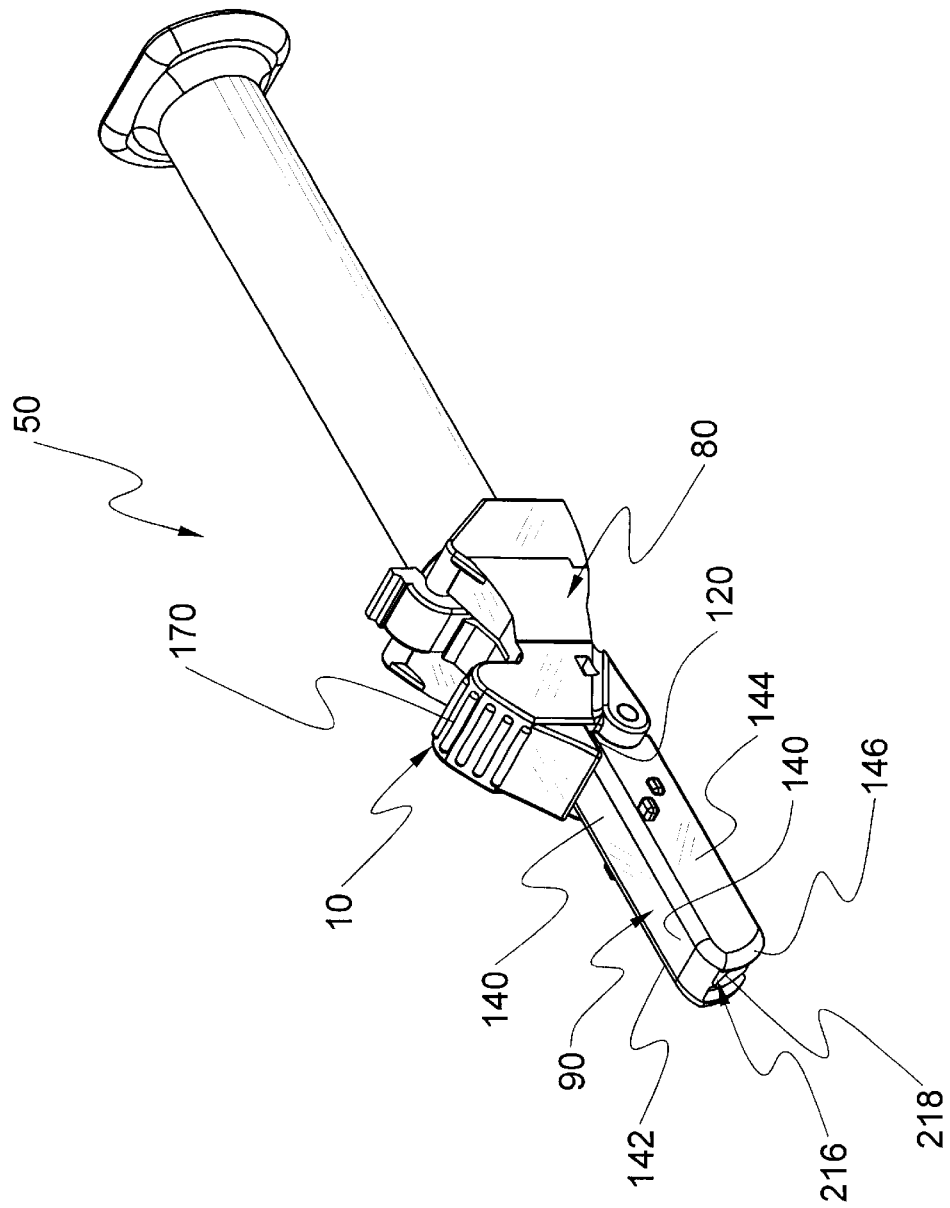
FIG. 4 is a perspective of the device seen in FIG. 3 with the safety shield fully unfolded to provide a safety sheath about the medical needle.
Figure 4A:
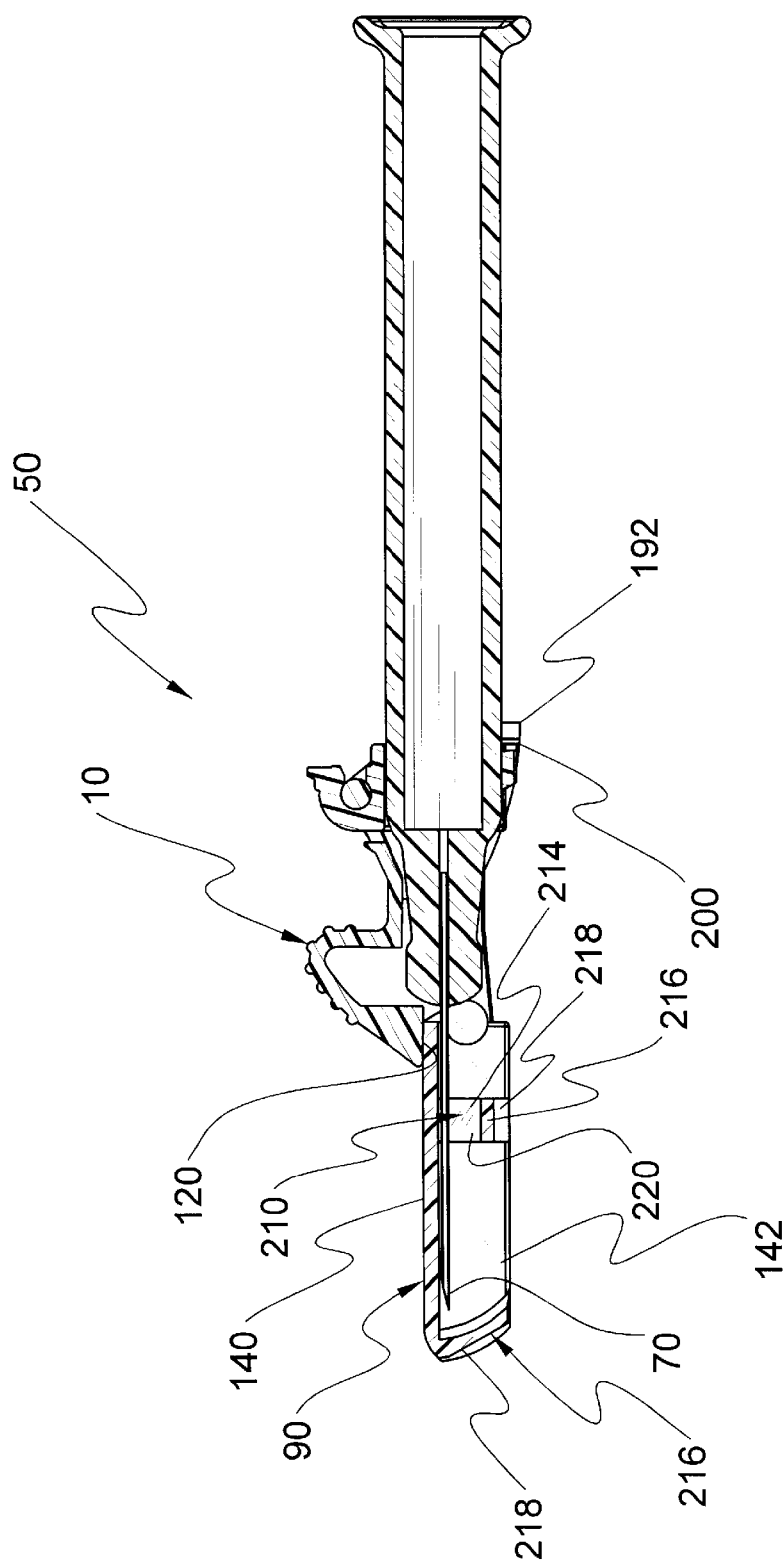
FIG. 4A is a cross section of a lateral elevation of the device as seen in FIG. 4.

Attention is now drawn to free end 146 of sheath member 90, see FIGS. 2A and 4 in particular. Note that sheath member 90 has two substantially planar, lateral sides 142 and 144 which terminate beyond an inwardly disposed section 216 at free end 146. As earlier mentioned, section 216 preferably comprises a closing surface 218, which provides further protection for needle tip 70 as seen in FIG. 4A. This depression of surface 218 relative to extending dimensions of sides 142 and 144 creates a track or slot in which needle 40 may be guided as shield 10 is unfolded and improves likelihood of proper operation of shield 10 during unfolding.

Figure 5:
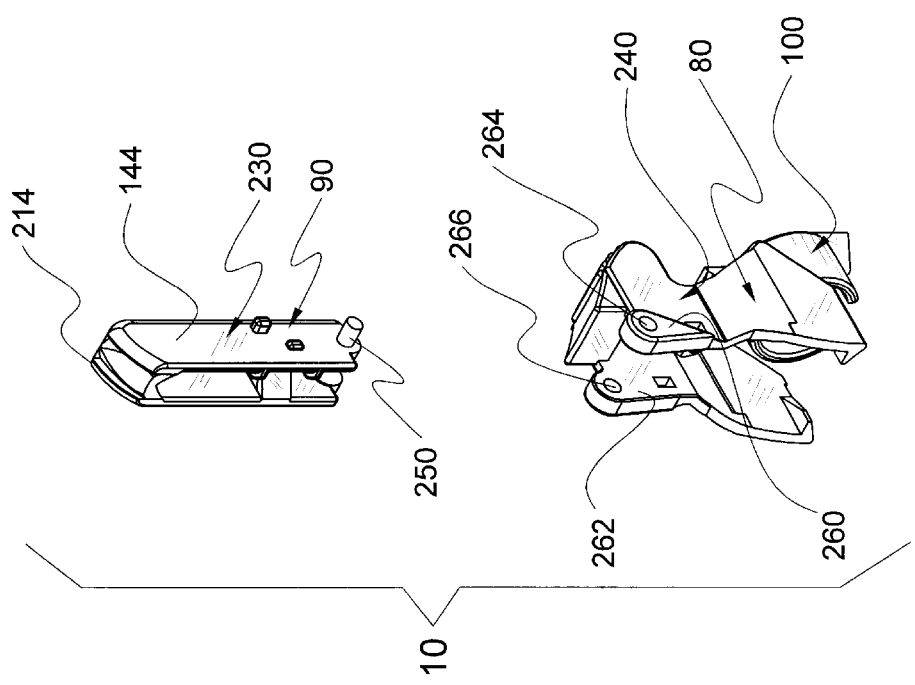
FIG. 5 is an exploded view of pre-assembled parts the safety shield.

As seen in exploded format in FIG. 5, shield 10 may be made from two injection molded parts, 230 and 240 although other molding configurations are possible, including making shield 10 from a single injection molded part. Part 230 is substantially made up of sheath member 90. Part 240 comprises connector assembly 100 and sheath member 80.

Currently, making shield 10 as two separate parts is preferred from a molding simplicity point of view. In this case hinge 102 (as seen in FIG. 2A) is a living hinge. Hinge part 130 is formed by a pair of outwardly protruding spindles (one of which is seen in FIG. 5 and which is numbered 250). A second spindle is juxtaposed spindle 250 on the opposite side 142 of sheath member 90.

Also, as seen in FIG. 5, part 240 has a pair of flattened appendages 260 and 262 each comprising a respective juxtaposed through hole 264 and 266. Appendages 260 and 262 are made to be sufficiently displaced to allow each spindle to be displaced into a respective hole 264 and 266, for example, spindle 250 into hole 266, thus forming hinge part 130, seen in FIG. 2A.

Both parts 230 and 240 are preferrably made from synthetic resinous material. Medical grade polypropylene is currently the material of preference due to cost, moldability and physical characteristics.

Figure 3A:
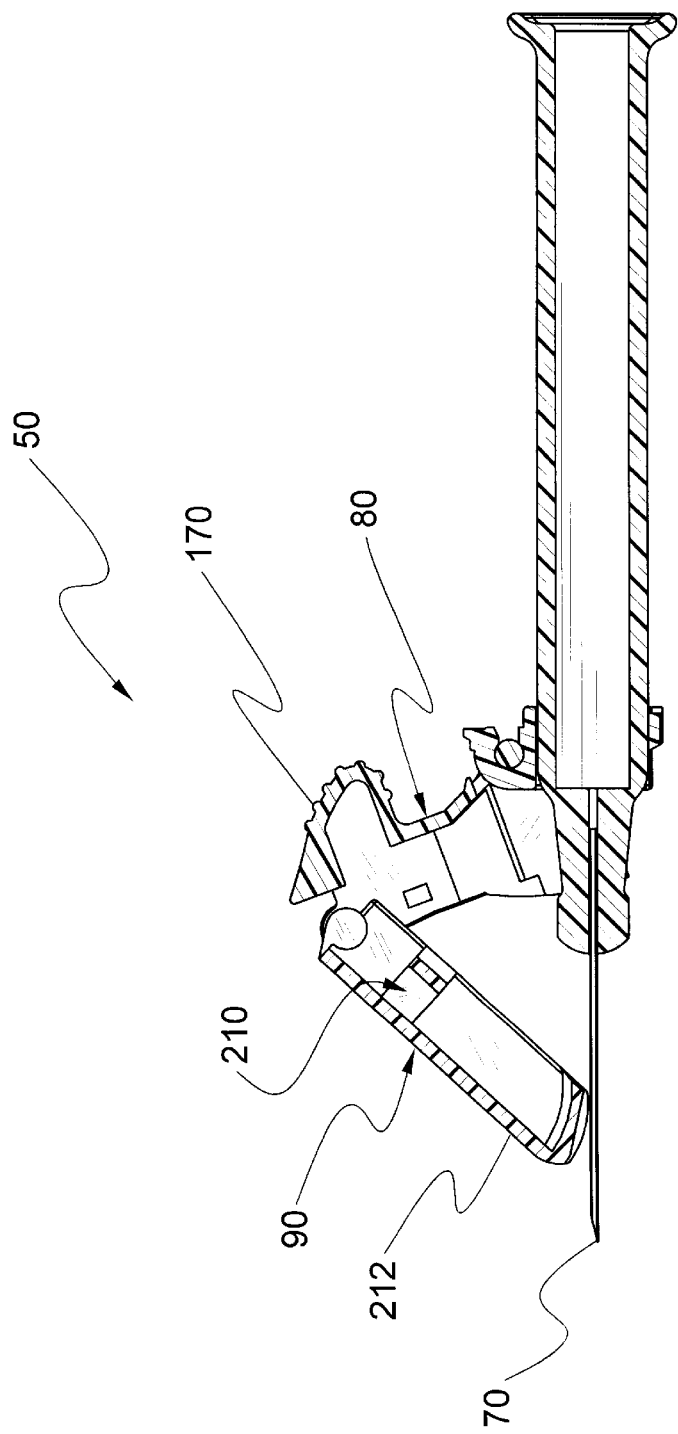
FIG. 3A is a cross section of a lateral elevation of the device as seen in FIG. 3.

From the folded state seen in FIGS. 2 and 2A, shield 10 is unfolded as seen in FIGS. 3, 3A, 4 and 4A, to ultimately be a safety shield for needle 40. To unfold shield 10, a distally directed force may be conveniently applied against button 170 which causes shield 10 to be displaced from the state seen in FIGS. 2 and 2A to an intermediate state as seen in FIGS. 3 and 3A. Note that an extended length of sheath member 90 relative to sheath member 80 causes free end 146 to be distally displaced ahead of hinge part 130. Such displacement prevents shield 10 from binding as it is unfolded. Even though such an extended length of sheath member 90 relative to sheath member 80 is important, other methods may be used to impede binding within the scope of the invention. (Further, note that a combined length of sheath members 80 and 90 must be long enough to enclose needle 40, but the combined length of sheath members 80 and 90 may be much longer than needle 40, thereby making possible use of a single injection molded part to satisfy needs of various lengths of needles.)

As free end 146 comes into contact with needle 40, a path of least resistance is along a track defined by surface 218, where it resides between sides 142 and 144, see FIG. 4. In this manner, sheath member 90 is controllably distally displaced until shield 10 completely unfolds and is unreleasibly latched to form a safety shield about needle 40 and needle tip 70 as seen in FIGS. 4 and 4A.

In addition to free end 146, a critical element of the invention disclosed herein is an interlock, in this case, formed by imposition of spur 120 upon side 140 of sheath member 90. As sheath members 80 and 90 unfold along needle 40, spur 120 is imposed upon top side 140 of sheath member 90 to form an interlock which makes sheath member 80 and sheath member 90 act as a single substantially rigid unit in combination with needle 40. So interlocked, this unit unreleasibly traps needle 40 and needle tip 70 in an enclosed, substantially rigid safety sheath. Without the interlock, shield 10 would be free to flex about hinge part 130, allowing flexure which might otherwise free needle 40 from being sheathed. Also, without the interlock, there would be no way to force sheath member 90 against needle 40 and thereby engage shield 10 as a safety enclosure.

The invention disclosed herein may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An unfoldable medical needle shield apparatus associated with a medical needle device which is folded into a compact state to permit access to a medical needle and an associated distally disposed sharpened tip for use in a medical procedure and unfolded and displaced about the medical needle to provide a protective safety sheath about at least the distally disposed sharpened tip of the medical needle, said shield apparatus comprising:
   a shield connector assembly whereby said needle shield apparatus is securely affixed to the medical needle device;
   a needle shield, hingeably affixed to said shield connector assembly, which provides the foldable portion of said apparatus, said shield comprising:
      a proximally disposed substantially rigid, elongated first sheath member comprising a first end at which said shield is hingeably affixed to said connector assembly such that said proximal sheath member rotates in-line with said medical needle when the shield is unfolded and extended and a second end which is distally disposed relative to the first end when the shield is unfolded;
      a substantially rigid, elongated second sheath member comprising a connected end hingeably affixed to the second end such that said second sheath member also rotates in-line with the medical needle when the shield is unfolded and an end free of connection to any other part when the shield is folded, said first sheathing member, in combination with said second sheathing member, comprising a length which extends along the length of the medical needle for safety when the shield is unfolded and at least the second sheath member being disposed about and sheathing the needle;
   at least one latch associated with the shield by which the shield is unreleasibly latched to be securely affixed in place relative to the medical needle and associated sharpened tip when the shield is unfolded and disposed about the needle; and
   an interlock which includes an outwardly extending, distally oriented spur of the second end that defines a first planar surface and a wall of the connected end that defines a second planar surface such that the second planar surface contacts the first planar surface in a flush engagement in a plane substantially parallel to a longitudinal axis of the needle such that said first sheath member and said second sheath member are forced into substantially rigid alignment with said needle as the shield is unfolded and securely latched as a safety sheath about the medical needle.

2. An unfoldable medical needle shield apparatus according to claim 1 wherein said second end comprises a spur which is a part of said interlock and by which the connected end is forced into alignment with the needle and rigidly held thereat as the shield is unfolded and securely latched.

3. An unfoldable medical needle shield apparatus according to claim 1 wherein said proximally disposed substantially rigid, elongated first sheath member further comprises a button which facilitates unfolding of the shield.

4. An unfoldable medical needle shield apparatus according to claim 1 wherein, in combination, said shield connector assembly and said proximally disposed substantially rigid, elongated first sheath member comprise a latch and catch which securely retains the shield apparatus when unfolded.

5. An unfoldable medical needle shield apparatus according to claim 1 wherein said connector assembly comprises structure whereby the needle shield apparatus is affixed to the device without impacting operational removal of a cover disposed about the medical needle and associated tip during storage and transport of the medical needle device before use.

6. An unfoldable medical needle shield apparatus according to claim 1 wherein said connection free end of said second sheath member comprises an exterior groove which acts as a track within which the medical needle glides as the needle shield is unfolded.

7. An unfoldable medical needle shield apparatus according to claim 1 wherein said second sheath member is longer than said first sheathing member to effectively impede binding as the needle shield unfolds.

8. A method for enclosing a sharpened medical needle in a safety shield comprising the steps of:
   providing a medical needle device comprising a hollow bore cannula securely affixed in a hub and aseptically covered by a needle cover, said cannula having at least one sharpened tip to form the medical needle, and a safety shield assembly which is hingeably joined to said hub of the medical needle device, said safety shield assembly comprising an elongated, foldable sheath which comprises a pair of serially interconnected substantially rigid segments each of which being interconnected to the adjacent segment by an intersegment hinge, a first segment comprising a free end which is unattached to any other portion of said part and a second segment, in combination with the first segment, comprising an interlock being disposed adjacent the intersegment hinge, the interlock including an outwardly extending, distally oriented spur of the second segment that defines a first planar surface and a wall of the first segment that defines a second planar surface such that the second planar surface is in a flush engagement with the first planar surface in a plane substantially parallel to a longitudinal axis of the needle, wherein the interlock acts about the intersegment hinge to force the segment with the free end against the needle as the sheath is unfolded and to force the segments into substantially rigid alignment with the needle, and comprising a channel in which at least a part of the cannula is disposed when the sheath is linearly extended, said foldable sheath and said hinges being disposed to permit folding of the sheath about the hub in a first state to permit usable access to said medical needle in a medical procedure and unfolding and extending of the sheath to a substantially planar disposition along said cannula whereat the cannula is disposed along the channel, said sheath further comprising at least one latching member which catches and securely affixes the sheath relative to the cannula, said sheath segments thereby forming a substantially rigid body which protectively encloses said sharpened tip and denies access thereto;

assembling the medical needle device without the safety shield assembly;

affixing the safety shield assembly to the medical needle device to form a safety medical needle device;

transporting and storing the safety medical needle device prior to use;

removing the safety medical needle device from storage preparatory for use;

removing the needle cover from the cannula and folded sheath, leaving the shield assembly in a compact state such that said needle tip is accessible for a medical procedure; and at the end of the medical procedure, displacing a proximal segment of said sheath to unfold segments of the sheath, forcing the interlock to cause the segments to jointly unfold until said at least latching member catches to form the substantially rigid body and thereby protectively enclose and deny access to said sharpened tip.

9. An unfoldable safety medical needle apparatus comprising:

a medical needle having a sharpened tip disposed on a distal end;

a removable needle cover which, in cooperation with a hub for said medical needle, is disposed about the medical needle to provide a fluid flow resistant seal for antiseptic purposes, said cover being removed for access to the medical needle for use in a medical procedure;

a safety shield assembly comprising:
 a safety sheath which is folded and compacted to permit the removable needle cover to be so disposed about the medical needle cover and to also permit access to the medical needle and associated distally disposed sharpened tip for use in a medical procedure and unfolded to be displaced about the medical needle to provide a protective safety sheath about at least the distally disposed sharpened tip;
 the medical needle hub in which a proximal end the medical needle is affixed;
 structure associated with the medical needle hub comprising connective geometry by which the needle cover is releasibly affixed to the medical needle hub and by which a proximally disposed fluid vessel is connected to the medical needle hub thereby providing fluid access between the vessel and said medical needle;
 a sheath connector assembly whereby the safety sheath is firmly affixed to said structure;
 the foldable needle sheath hingeably affixed to the sheath connector assembly, said sheath comprising:
  a proximally disposed substantially rigid, elongated first sheath member comprising a first end at which said sheath is hingeably affixed to said connector assembly such that said proximal sheath member rotates in-line with said medical needle when the sheath is unfolded and extended and a second end which is distally disposed relative to the first end when the sheath is unfolded;
  a substantially rigid, elongated second sheath member comprising a connected end hingeably affixed to the second end such that said second sheath member also rotates in-line with the medical needle when the sheath is unfolded and an end free of connection to any other part, said first sheath member in combination with said second sheath member comprising a length which extends completely along the medical needle such that at least the second sheath member provides a sheath which shields at least the sharpened tip of the medical needle for safety when the sheath is unfolded;
  at least one latch associated with the shield by which the sheath is unreleasibly latched to be securely affixed in place relative to the medical needle and associated sharpened tip when the sheath is unfolded about the needle; and
  an interlock which includes an outwardly extending, distally oriented spur of the second end that defines a first planar surface and a wall of the connected end that defines a second planar surface such that the second planar surface contacts the first planar surface in a flush engagement in a plane substantially parallel to a longitudinal axis of the needle such that said first sheath member and the second sheath member are forced into substantially rigid alignment with said needle to be securely latched as a safety shield about the medical needle as the sheath is unfolded.

10. A medical needle apparatus comprising:

a connector portion having a needle extending therefrom; and a needle shield being extensible between a retracted position and an extended position, the needle shield including:
 a substantially rigid first sheath member having a first end hingedly affixed to the connector portion and a second end defining an outwardly extending, distally oriented spur having a first planar surface; and
 a substantially rigid second sheath member having a connected end hingedly affixed to the second end and a free end, the connected end defining a wall having a second planar surface;
 in the extended position, the second planar surface contacting the first planar surface in a flush engagement in a plane substantially parallel to a longitudinal axis of the needle such that the first sheath member and second sheath member are forced into a substantially rigid alignment to enclose the needle.

11. A medical needle apparatus as recited in claim 10, wherein the second sheath member has a top wall and a pair of laterally disposed walls extending from the top wall, the top wall having the second planar surface.

12. A medical needle apparatus as recited in claim 10, wherein the first sheath member and the second sheath member include latching structure for releasably fixing the needle shield in the retracted position.

13. A medical needle apparatus as recited in claim 10, wherein the first sheath member includes a wing that engages a catch of the connector portion to unreleasably fix the needle shield in the extended position.

14. A medical needle apparatus as recited in claim 10, wherein the first sheath member includes a pair of inward projecting wings that rotate relative to the connector portion to engage an edge of the connector portion to unreleasably fix the needle shield in the extended position.

15. A medical needle apparatus as recited in claim 10, wherein the second sheath member has an interior clip configured to engage the needle to fix the needle shield in the extended portion.

* * * * *